US008417467B2

(12) United States Patent
Nelson

(10) Patent No.: US 8,417,467 B2
(45) Date of Patent: Apr. 9, 2013

(54) SHIELDING AND ACTIVITY ESTIMATOR FOR TEMPLATE-BASED NUCLIDE IDENTIFICATION METHODS

(75) Inventor: Karl Einar Nelson, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 217 days.

(21) Appl. No.: 12/770,260

(22) Filed: Apr. 29, 2010

(65) Prior Publication Data
US 2011/0270536 A1 Nov. 3, 2011

(51) Int. Cl.
G01N 31/00 (2006.01)
G01T 1/178 (2006.01)
(52) U.S. Cl. .................. 702/30; 250/370.03
(58) Field of Classification Search ............... 702/30, 702/23, 26–29, 31–32, 40, 66–67, 70–73, 702/75–76, 78, 81, 84, 127–129, 137, 170, 702/172–173, 179–180, 182–183, 189–190, 702/194, 196; 376/153–154, 156–157, 180–182, 376/193; 378/4–5, 82–83, 86, 88–90; 250/370.03, 250/370.05–370.07, 370.09, 370.11, 390.02–390.04, 250/390.06–390.07, 390.11, 394; 703/2, 703/5, 12
See application file for complete search history.

(56) References Cited

U.S. PATENT DOCUMENTS
2011/0270575 A1* 11/2011 Nelson ......................... 702/181

OTHER PUBLICATIONS

Burr et al., Radio-Isotope Identification Algorithms for NaI Gamma Spectra, Mar. 3, 2009, Algorithms 2009, pp. 339-360.*
Arnold et al., The 2002 IAEA Intercomparison of Software for Low-Level Gamma-Ray Spectrometry, 2005, Nuclear Instruments and Methods in Physics Research A 536, 2005, pp. 196-210.*
O. Marzocchi, Automation of a Gamma Spectrometric Analysis Method for Naturally Occuring Radionuclides in Different Materials (NORM), Jun. 2009, Institut fur Strahlenforschung, 92 pp.*
Non-Final Office Action Summary from U.S. Appl. No. 12/770,215 dated Feb. 22, 2012.
Gosnell, T., "Automated Calculation of Photon Source Emission from Arbitrary Mixture of Naturally Radioactive Heavy Nuclides," 1990, Nuclear Instruments and Methods in Physics Research A 299, pp. 682-686.
Roemer et al., "Simulation of Template Spectra for Scintillator Based Radionuclide Identification Devices Using GEANT4," 2006 IEEE Nuclear Science Sumposium Conference Record, pp. 247-252.
Non-Final Office Action Summary from U.S. Appl. No. 12/770,215 dated Jul. 24, 2012.

(Continued)

Primary Examiner — Toan Le
(74) Attorney, Agent, or Firm — Dominic M. Kotab

(57) ABSTRACT

According to one embodiment, a method for estimating an activity of one or more radio-nuclides includes receiving one or more templates, the one or more templates corresponding to one or more radio-nuclides which contribute to a probable solution, receiving one or more weighting factors, each weighting factor representing a contribution of one radio-nuclide to the probable solution, computing an effective areal density for each of the one more radio-nuclides, computing an effective atomic number (Z) for each of the one more radio-nuclides, computing an effective metric for each of the one or more radio-nuclides, and computing an estimated activity for each of the one or more radio-nuclides. In other embodiments, computer program products, systems, and other methods are presented for estimating an activity of one or more radio-nuclides.

20 Claims, 7 Drawing Sheets

OTHER PUBLICATIONS

O. Marzocchi, "Automation of a Gamma Spectrometric Analysis Method for Naturally Occurring Radionuclides in Different Materials (NORM)," Jun. 2009, Institut fur Strahlenforschung, 92 pp.

Notice of Allowance and Fee(s) Due from U.S. Appl. No. 12/770,215 dated Dec. 21, 2012.

* cited by examiner

SHIELDING AND ACTIVITY ESTIMATOR FOR TEMPLATE-BASED NUCLIDE IDENTIFICATION METHODS

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to radio-nuclide identification, and particularly, to estimating shielding and activity for template-based nuclide identification methods.

BACKGROUND

Automated template-based nuclide identification methods have been under development in recent years. These methods improve accuracy over conventional methods by making better use of spectral information than peak analysis methods. However, these template-based methods are currently limited to identifying the nuclide along with perhaps a very rough estimate of the shielding (e.g., light shielding, heavy shielding, etc.). Internally, the method has solved for some linear combination that could sum to produce the observed spectrum, but this is insufficient to determine the configuration which produced the radiation. To solve for the shielding information, a representation of the physics-based model is constructed (typically one dimensional) and then transported using a radiation transport code. This operation generally requires a human in the loop, since indentifying the correct starting point for optimization is difficult to accomplish with automated methods. Thus, conventional template-based methods cannot be applied to automated instruments as part of the alarming method, nor can they be applied in the field by first responders (e.g., using handheld devices).

Therefore, it would be beneficial to the field of radio-nuclide identification to be able to identify radio-nuclides along with any shielding and activity information that are also capable of avoiding the problems associated with conventional techniques.

SUMMARY

In one embodiment, a method for estimating an activity of one or more radio-nuclides includes receiving one or more templates, the one or more templates corresponding to one or more radio-nuclides which contribute to a probable solution, receiving one or more weighting factors, each weighting factor representing a contribution of one radio-nuclide to the probable solution, computing an effective areal density for each of the one more radio-nuclides, computing an effective atomic number (Z) for each of the one more radio-nuclides, computing an effective metric for each of the one or more radio-nuclides, and computing an estimated activity for each of the one or more radio-nuclides.

In another embodiment, a computer program product for estimating an activity of one or more radio-nuclides includes a computer readable memory having computer readable code stored thereon. The computer readable code is configured to: receive one or more templates, the one or more templates corresponding to one or more radio-nuclides which contribute to a probable solution, receive one or more weighting factors, each weighting factor representing a contribution of one radio-nuclide to the probable solution, compute an effective areal density for each of the one more radio-nuclides, compute an effective atomic number (Z) for each of the one more radio-nuclides, compute an effective metric for each of the one or more radio-nuclides, and compute an estimated activity for each of the one or more radio-nuclides.

In yet another embodiment, a system for estimating an activity of one or more radio-nuclides includes a processor, a computer readable memory, and logic, which when executed by the processor causes the system to: receive one or more templates, the one or more templates corresponding to one or more radio-nuclides which contribute to a probable solution, receive one or more weighting factors, each weighting factor representing a contribution of one radio-nuclide to the probable solution, compute an effective areal density for each of the one more radio-nuclides by: calculating an areal density biasing coefficient for each of the one or more templates; multiplying together the weighting factor for each of the one or more radio-nuclides, the areal density biasing coefficient for each of the one or more templates, and an areal density corresponding to each of the one or more template to obtain a value; and dividing the value by a sum of the weighting factors for each of the one or more radio-nuclides multiplied by the areal density biasing coefficient for each of the one or more templates, compute an effective atomic number (Z) for each of the one more radio-nuclides by calculating an effective atomic number (Z) biasing coefficient for each of the one or more radio-nuclides; multiplying, for each of the one or more radio-nuclides, the weighting factor by the effective atomic number (Z) biasing coefficient by an atomic number (Z) corresponding to each of the one or more templates to obtain a value; and dividing the value by a sum of the weighting factors for each of the one or more radio-nuclides multiplied by the effective atomic number (Z) biasing coefficient, compute an effective metric for each of the one or more radio-nuclides by summing each of the effective metrics multiplied by the weighting factor for each of the one or more radio-nuclides, and compute an estimated activity for each of the one or more radio-nuclides by dividing the effective metric by a metric per unit activity to calculate the estimated activity for the one or more radio-nuclides.

Other aspects and embodiments of the present invention will become apparent from the following detailed description, which, when taken in conjunction with the drawings, illustrate by way of example the principles of the invention.

DETAILED DESCRIPTION

Figure 1:
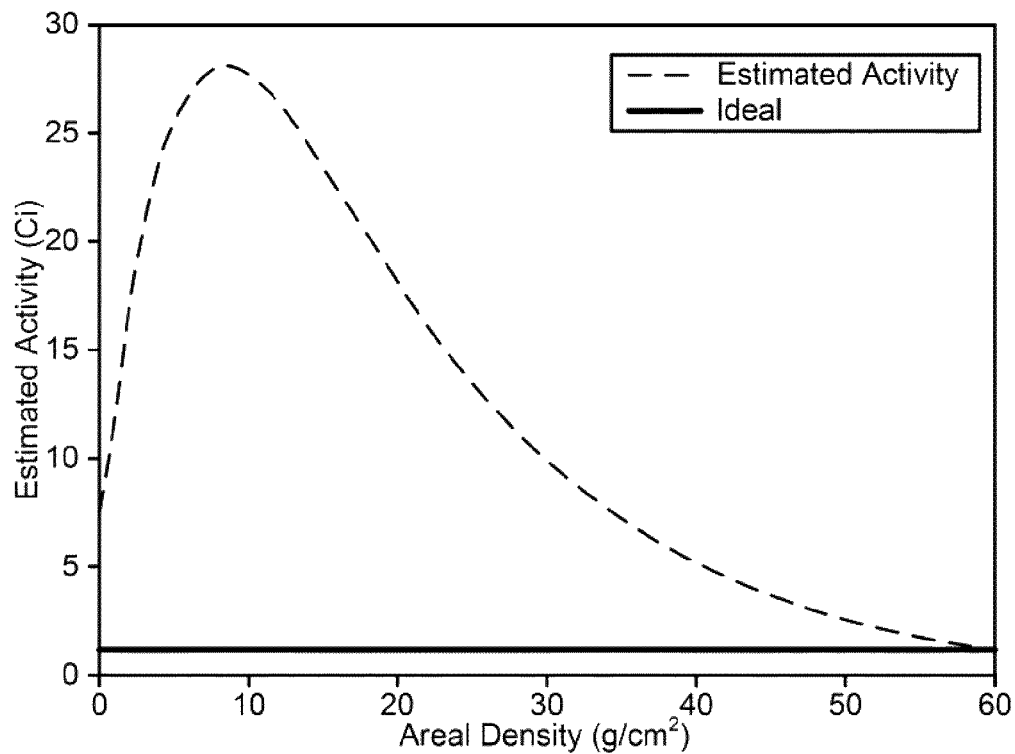
FIG. 1 includes plots of estimated activity and areal density versus truth as a function of areal density, according to experimental results.
Figure 1:
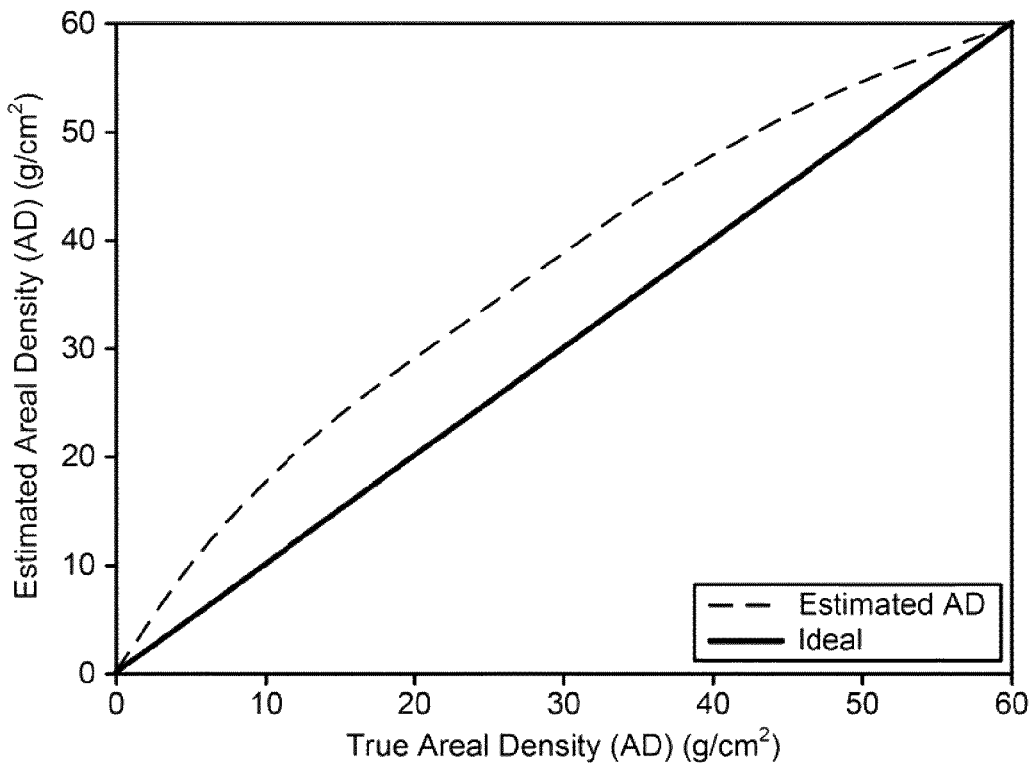

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

As used herein, the term "about" when combined with a value refers to plus and minus 10% of the reference value unless otherwise specified. For example, a temperature of about 50° C. refers to a temperature of 50° C.±5° C., etc.

The description herein is presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

In particular, various embodiments of the invention discussed herein are implemented using the Internet as a means of communicating among a plurality of computer systems. One skilled in the art will recognize that the present invention is not limited to the use of the Internet as a communication medium and that alternative methods of the invention may accommodate the use of a private intranet, a Local Area Network (LAN), a Wide Area Network (WAN) or other means of communication. In addition, various combinations of wired, wireless (e.g., radio frequency) and optical communication links may be utilized.

The program environment in which one embodiment of the invention may be executed illustratively incorporates one or more general-purpose computers or special-purpose devices such hand-held computers. Details of such devices (e.g., processor, memory, data storage, input and output devices) are well known and are omitted for the sake of clarity.

It should also be understood that the techniques of the present invention might be implemented using a variety of technologies. For example, the methods described herein may be implemented in software running on a computer system, or implemented in hardware utilizing either a combination of microprocessors or other specially designed application specific integrated circuits, programmable logic devices, or various combinations thereof. In particular, methods described herein may be implemented by a series of computer-executable instructions residing on a storage medium such as a physical computer-readable medium. In addition, although specific embodiments of the invention may employ object-oriented software programming concepts, the invention is not so limited and is easily adapted to employ other forms of directing the operation of a computer.

The invention can also be provided in the form of a computer program product comprising a physical computer readable medium having computer code thereon. A computer readable medium can include any physical medium capable of storing computer code thereon for use by a computer, including optical media such as read only and writeable CD and DVD, magnetic memory, semiconductor memory (e.g., FLASH memory and other portable memory cards, etc.), etc.

Disclosed herein, according to some embodiments, are methods and devices that can utilize the information from a template matching algorithm to reasonably create an accurate estimate of the shielding configuration and the source activity. This can then be used in automated routines for alarming, in handheld detectors for first responders, and/or to provide the initial model for a more detailed analysis.

In some approaches, the methods disclosed herein combine the estimated regression coefficients with a set of predetermined mixing weights to compute the shielding configuration using an electrical conductance based model. The methods then compute the radiation exposure dose for the measurement. Then, by using the estimated shielding parameters, the methods can look up the dose to activity factor typically used in radiation exposure for personnel protection. The combination of the dose estimate with the dose to activity factor produces a reasonably accurate activity estimate suitable for alarming. The shielding estimate can also be used as a starting point for building a more elaborate physics based model.

In one general embodiment, a method for estimating an activity of one or more radio-nuclides includes receiving one or more templates, the one or more templates corresponding to one or more radio-nuclides which contribute to a probable solution, receiving one or more weighting factors, each weighting factor representing a contribution of one radio-nuclide to the probable solution, computing an effective areal density for each of the one more radio-nuclides, computing an effective atomic number (Z) for each of the one more radio-nuclides, computing an effective metric for each of the one or more radio-nuclides, and computing an estimated activity for each of the one or more radio-nuclides.

In another general embodiment, a computer program product for estimating an activity of one or more radio-nuclides includes a computer readable memory having computer readable code stored thereon. The computer readable code is configured to: receive one or more templates, the one or more templates corresponding to one or more radio-nuclides which contribute to a probable solution, receive one or more weighting factors, each weighting factor representing a contribution of one radio-nuclide to the probable solution, compute an effective areal density for each of the one more radio-nuclides, compute an effective atomic number (Z) for each of the one more radio-nuclides, compute an effective metric for each of the one or more radio-nuclides, and compute an estimated activity for each of the one or more radio-nuclides.

In yet another general embodiment, a system for estimating an activity of one or more radio-nuclides includes a processor, a computer readable memory, and logic, which when executed by the processor causes the system to: receive one or more templates, the one or more templates corresponding to one or more radio-nuclides which contribute to a probable solution, receive one or more weighting factors, each weighting factor representing a contribution of one radio-nuclide to the probable solution, compute an effective areal density for each of the one more radio-nuclides by: calculating an areal density biasing coefficient for each of the one or more templates; multiplying together the weighting factor for each of the one or more radio-nuclides, the areal density biasing coefficient for each of the one or more templates, and an areal density corresponding to each of the one or more template to obtain a value; and dividing the value by a sum of the weighting factors for each of the one or more radio-nuclides multiplied by the areal density biasing coefficient for each of the one or more templates, compute an effective atomic number (Z) for each of the one more radio-nuclides by calculating an effective atomic number (Z) biasing coefficient for each of the one or more radio-nuclides; multiplying; for each of the one or more radio-nuclides, the weighting factor by the effective atomic number (Z) biasing coefficient by an atomic number (Z) corresponding to each of the one or more templates to obtain a value; and dividing the value by a sum of the weighting factors for each of the one or more radio-nuclides multiplied by the effective atomic number (Z) biasing coefficient, compute an effective metric for each of the one or more radio-nuclides by summing each of the effective metrics multiplied by the weighting factor for each of the one or more radio-nuclides, and compute an estimated activity for each of the one or more radio-nuclides by dividing the effective metric by a metric per unit activity to calculate the estimated activity for the one or more radio-nuclides.

Automated gamma-ray spectrum analysis to identify radioactive materials is used for a broad range of national security missions. Protection against terrorists utilizing radioactive materials and the need to monitor operations with nuclear materials operations to prevent proliferation of nuclear weapons are two possible areas of application. To combat nuclear smuggling threats, the United States has deployed gamma and neutron radiation portal monitors and handheld detectors as part of a boarder protection strategy. The gamma detectors typically include energy-sensitive scintillation materials that collect photons in order to produce a histogram of pulse energy often referred to as a gamma ray spectrum. Analysis algorithms process this spectrum to identify radioactive materials. This problem is challenging due to the variety of spectral shapes that are produce by radio-nuclide when coupled with detector resolution, detector calibration drift, source shielding, and environmental scattering, among other influences.

Unfortunately, known methods used to analyze spectral data are not well documented in the open literature. Commercial vendors that produce algorithms for their instruments are reluctant to share details of their algorithmic approaches. Academic algorithms are openly published, but are generally confined to simplified problems such as the identification of bare materials using laboratory-calibrated instruments. Government-developed algorithms are often used by analysts, but details of the performance and capabilities of the algorithms used may be restricted due to security concerns.

Because of these limitations, there are few descriptions of algorithms that are sufficiently robust to operate on field instruments. This poses a significant problem in modeling and comparing the performance of systems, which is needed to identify the best alternative to select for deployment. Therefore, to more accurately predict system performance, a complete analysis system that includes all of the elements for robust identification has been developed, according to some embodiments. One embodiment of the system and code implementation is referred to as the Radio-Nuclide Analysis Kit (RNAK). For simplicity, the descriptions of embodiments and approaches presented herein may be referred to in the context of functionality of a RNAK system. However, the embodiments are not so limited, as they may be used in any desired environment, and are not limited to simply being applied to spectral analysis, but may also be used in other fields as well, such as astronomy, nuclear physics, etc.

One aspect of a RNAK system which may be used to more effectively determine an unknown radio-nuclide is the method used to estimate the source activity and surrounding shielding materials. Activity and shielding are key parameters used to decide whether a source is insignificant or poses a serious threat in nuclear smuggling applications. The methods presented herein are one possible implementation used to estimate these quantities, and are representative of other methods that may be applied in other embodiments.

Identification Algorithm

Before presenting details of the estimation methods, the framework used to perform the initial analysis is presented. Radio-nuclide identification methods, according to some embodiments, generally use one of two approaches to identify sources.

The first is peak extraction and analysis. In peak analysis, one routine extracts the relative intensity and energy of each photo peak in the spectrum. This extracted list of peaks and energies is then processed through a system which finds a combination of sources which could have produced the observation. Ratios of peaks can be used to identify shielded sources using Beer's law for sources with multiple emitted energies. However, this approach cannot determine shielding for monoenergetic sources.

The second analysis approach is to use multiple linear regression to find some combination of pre-computed templates that best fits the observed spectrum. This approach is more powerful because the algorithm makes more complete use of the spectral information, including such features as Compton edges and the shape of the continuum. However, it is also more challenging to apply as template matching must account for all of the processes that produce spectral shape and the necessary templates must be available for the regression analysis.

The identification algorithm in RNAK, according to one embodiment, utilizes the template analysis approach. The algorithm includes all of the elements including calibration, feature extraction, sample covariance estimation, regression, multiple solution weighting, and parameter estimation. First, calibration consists of an algorithm to extract peak locations from a reference spectrum taken prior to the sample and an adjustment to the energy calibration curve such that the energy of the observed spectrum will match the calibration used to construct the templates. Next, feature extraction takes the calibrated spectrum and converts it to a representation which preserves the spectral features while removing extraneous statistical noise. The sample covariance estimation algorithm computes the statistical and systematic noise based on the observed spectrum, background spectrum, accuracy of the energy calibration, and the linear transform used in the feature extraction. The multiple linear regression algorithm then evaluates the best fit (least errors fit) between the templates and the observation using this covariance matrix. The regression algorithm is called multiple times using different sets of templates to evaluate alternative possible solutions. The mixture analysis algorithm directs the search through the tree of possible solutions and weights the mixtures by fitness, model complexity, and prior source frequency estimates that are characteristic of the monitored population of objects. Methods of tree pruning similar to branch and bound may be used to identify branches that do not include better solutions relative to solutions already considered. Once this tree has been explored, the best set of solutions is passed the parameter estimation routines, which compute important physical properties such as the activity, effective atomic number (Z) of the shielding material, and the effective areal density (density times thickness) of intervening materials. The results of this analysis are then provided to an alarming algorithm, which is dictated by the application.

An example of obtaining contributions of radio-nuclides is provided in copending U.S. patent application Ser. No. 12/770,215, filed concurrently herewith to Karl Nelson and having the title "Radio-Nuclide Mixture Identification Using Medium Energy Resolution Detectors." Of course, any other suitable method may be used, and the methods disclosed herein are not limited to being used with the methods disclosed in copending U.S. patent application Ser. No. 12/770, 215.

To perform this source identification task, the algorithm uses a template library. Many templates are used to describe each radio-nuclide as the template library spans the range of shielding materials both in terms of areal density and atomic number. Nuclides that produce gamma rays with multiple energies use more templates as each gamma ray line has different attenuation coefficients through attenuating materials. More templates allow for a better fit, but also increase the time for the analysis to complete (a concern for automated implementation in high-throughput applications). Because computation time of the tree-exploring and regression algorithms scale roughly as $O(n^3)$ with the number of templates, library designers generally are forced to construct the most compact representation possible for each radio-nuclide. That is, for a given maximum counts produced from the source, the library may be a minimal set such that all samples in the described space fit a linear combination of templates with the desired statistical confidence. This sparse description will complicate the task of the parameter estimation routine.

For simplicity, only the parameter estimation algorithms are considered herein. Accordingly, the algorithm is simplified to remove unnecessary components, such as the tree search, in some approaches. Also, for illustration of the methods, a single radio-nuclide is used at a time. Thus, the regression results for templates are analyzed that correspond to that radio-nuclide. The feature extraction includes a transform from linear energy binning to quadratic-spaced energy bins. This ensures that energy peaks at lower energies occupy the same number of energy bins as higher energy peaks once the detector energy resolution has been applied. All spectra are computed synthetically using a detector response code available in the GADRAS, and are assumed to have perfect energy calibration. The regression algorithm used is a non-negative least means squared algorithm with a step wise subset selection. As calibration errors have not been included and the standard statistic assumption is that each channel is an independent Poisson variable, only the diagonal elements of the covariance matrix are calculated, in some approaches.

The variance in each channel is given as a function of the number of counts in that channel $y_i$. The simplified expression $\sigma_{ii}^2 = 1 + y_i + \alpha y_i^2$ for diagonal variance terms is used, in some approaches. The offset and the linear term are derived from expected variance for a Poisson random variable. The quadratic term accounts for systematic errors which increase proportionally to the square of the counts.

Naïve Parameter Estimation

Given a spectrum for a given radio-nuclide, the expression $Ax=Y$ has been solved where A is the library of templates (also known as the regressors), x are the regression coefficients, and Y is the observation. Associated with each regressor $A_i$ are the scalar quantities activity per count ($Q_i$), dose per count ($D_i$), effective Z ($Z_i$), and effective areal density ($\rho l_i$). One goal is to estimate these same properties for the observation. Each regressor is normalized to have a $l_1$ norm equal to one. Thus the regression coefficient is equal to the number of counts in the observation for that regressor. From the regression coefficients, four critical quantities are calculated: dose, activity, effective Z, and effective areal density. The dose and activity are proportional to the number of counts and thus the naïve equation expected would be Equation 1, below. However, the shielding parameters are not proportional to the counts and thus would be naïvely estimated using a weighted average. The areal density and the effective Z are computed based on the weighted fraction of counts times the corresponding scalar quantity (generically written as $V_i$) as shown in Equation 2.

$$\tilde{Q} = \sum_n Q_t x_t \qquad \text{Equation 1}$$

$$\tilde{V} = \frac{\sum_t^u V_t x_t}{\sum_j^u x_j} \qquad \text{Equation 2}$$

Unfortunately, neither of these equations produces satisfactory results in practice. Activity estimates for $^{137}$Cs are generally biased high and have a range over two orders of magnitude for sources with the same activity. Shielding estimates are similarly poor. Areal density is estimated to be too high except in the immediate vicinity of modeled templates. Effective Z is uniformly estimated to be too low. Only the dose from source when calculated using Equation 1 is accurate.

To illustrate why this naïve approach fails, the simplified problem in which a $^{137}$Cs source is to be identified that is shielded with a spherical lead shell is considered. For this simplified problem, two templates would be used to fit the expected range of variability for this source. Estimates of activity and areal density would be as shown in FIG. 1. These estimates are plotted in the noise free case where the best estimate would have been produced.

Figure 2:
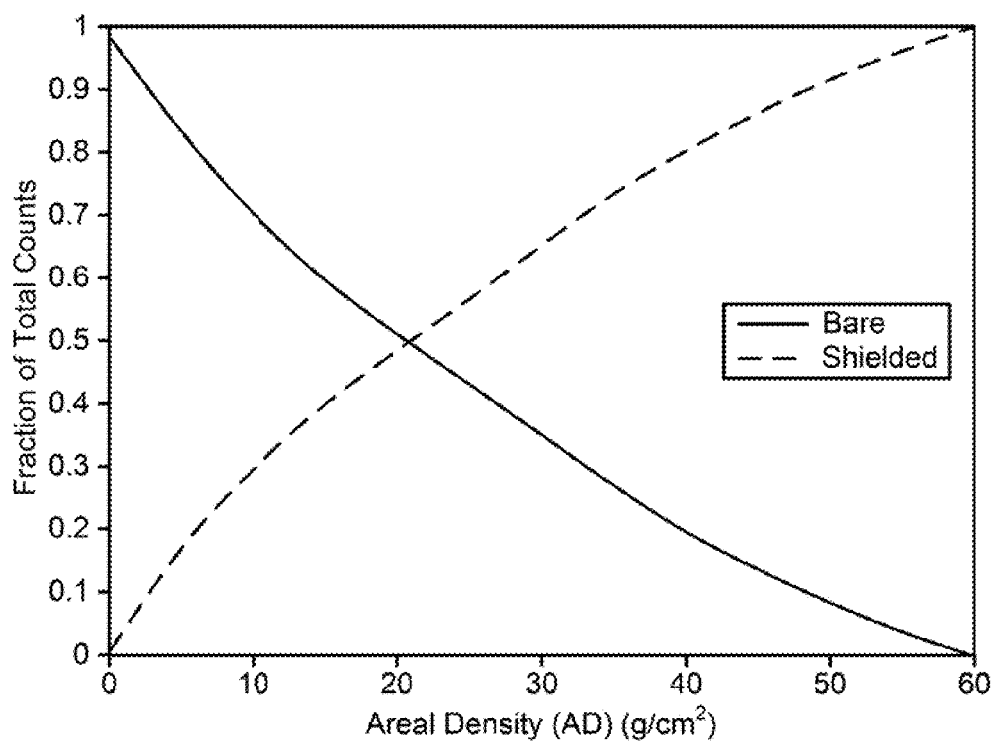
FIG. 2 is a plot of relative template weights as a function of areal density for $^{137}$Cs regression with two templates, according to experimental results.

The fraction of counts contributed by each regressor can be plotted as a function of the areal density as shown in FIG. 2. For the bare and heavily shielded case, the fraction of counts contributed is one in the corresponding regressor as expected. However, the distribution of counts for areal densities between is not linear with areal density. The fraction of counts is biased toward the more heavily shielded model. This corresponded to an overestimate of the dose and activity.

Although the monenergetic source used in this example seems simplistic, it is actually the most challenging type of source to identify properly. As was mentioned earlier, shielding around multiline sources can be estimated using Beer's law and the differential shielding coefficients of the absorber. Also, the number of templates can be increased such that the deviation between interpolated points is arbitrarily small. However, this is not done in practice as compact representations are required for speed.

Circuit View of Parameter Estimation

Figure 3:
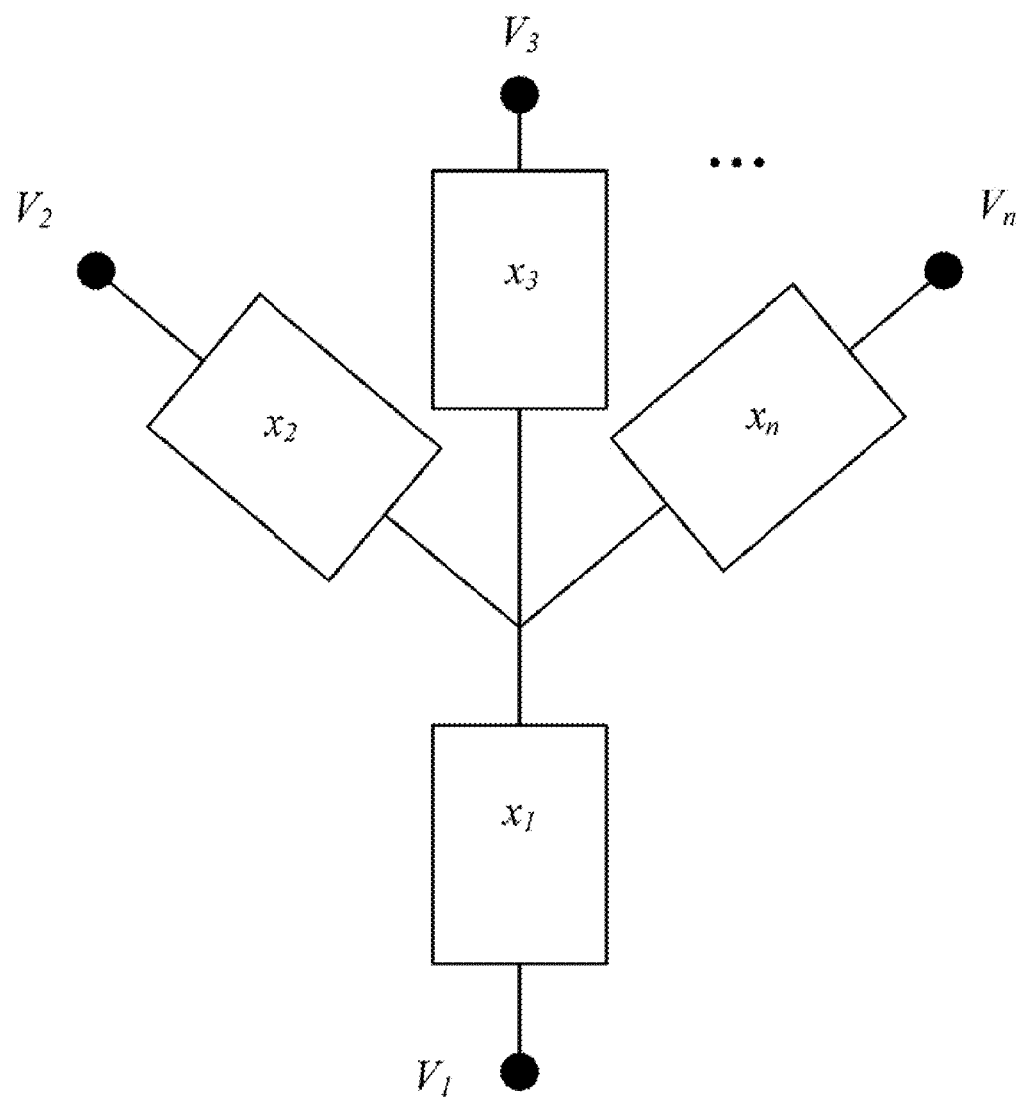
FIG. 3 is a circuit diagram corresponding to Equation 3 which interpolates the scalar quantities associated with each template to the scalar quantity corresponding to the observation, according to one embodiment.

An alternative interpolation algorithm is now proposed. The counts in the regression were biased towards the heavily shielded source and therefore the interpolation algorithm is modified to compensate. The alternative lies in interpreting the naïve interpolation equation as an analogous electrical circuit. Equation 2 could be viewed as computing the voltage on a node which is connected to a set of voltage sources through a resistor whose conductance value is $x_i$ as in the classic Wye circuit shown in FIG. 3. In FIG. 3, the connections between the members are conductance. The choice of these resistors $(x_1, x_2, x_3, \ldots, x_n)$ is arbitrary and thus the conductance may be set to any function $f_i(x_i)$. The simplest would be to set the conductance to be the regression coefficient times a linear factor $\omega_i$. This is referred to as the attraction factor. The greater the attraction factor, the more the estimated quantity will be drawn to the corresponding value of the regressor.

To use this model, the attraction for each regressor is computed relative to the others. These coefficients can be computed by simulating a large set of samples with the desired region of interpolation and then fitting the attractors to minimize the error. This is best done by applying the Nelder-Mead method to an optimizating problem given as follows. The Nelder-Mead method can solve a set of joint optimization for all training samples given by the Equation 3.

$$b_i \sum_j w_j x_{ij} = \sum_j w_j v_j x_{ij} \quad \text{Equation 3}$$

In Equation 3, $x_{ij}$ is the j th regressor in the i th training sample, $w_j$ is the attractor corresponding to j th regressor, $v_j$ is the true value of the physical constant corresponding to the j th regressor, and $b_i$ is the true value for the i th training sample.

One thousand random samples were drawn from the population to be interpolated for training. This procedure works very well to estimate the areal density of the sample even when noise is included. Computation of Z, on the other hand, produces inconsistent results using this method. The only insight that this method provides is that the bare template should have little weight in deciding what the Z should be as the Z of the bare source is undefined. All of the other templates should be weighted equally. Alternative expressions have been considered to estimate Z from the regression coefficients but none have performed significantly better than the basic weighted sum.

Demonstration of Shielding Estimates

Figure 4:
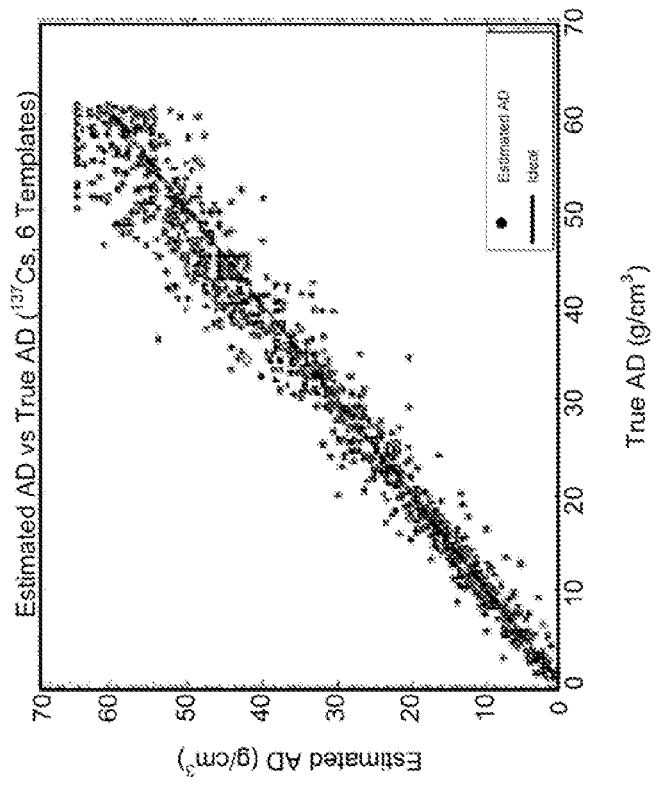
FIG. 4 includes plots of estimated Z and areal density versus truth for Monte Carlo evaluation with noise, according to experimental results.
Figure 4:
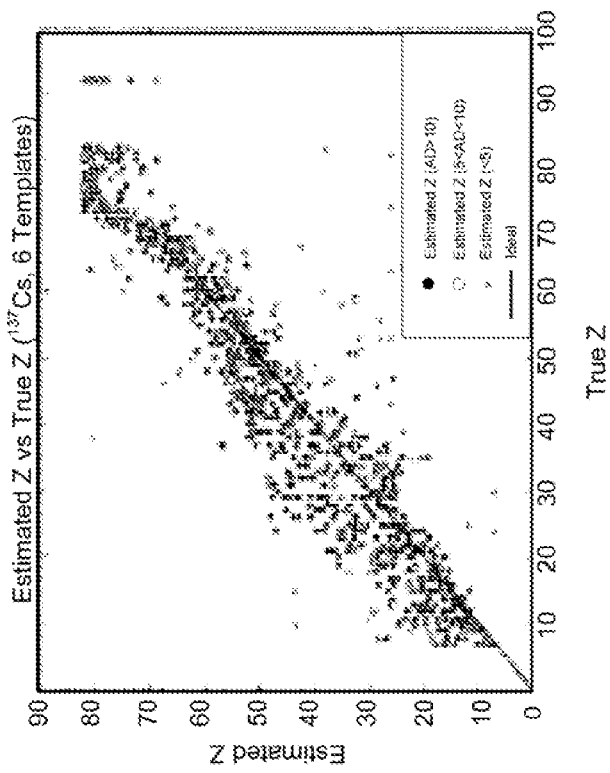

To demonstrate the performance of this algorithm, a Monte Carlo evaluation of the shielding estimators on a range of $^{137}$Cs samples was performed. Results of this evaluation appear in FIG. 4, which shows the estimated Z and real areal density versus true values for Monte Carlo evaluation with noise. Samples were drawn from an effective Z ranging from 7 to 82 plus 92 to represent depleted uranium. The areal density ranged from 1 to 60 g/cm². The template library included $^{137}$Cs samples ranging from 0 to 60 g/cm² with a fixed set of Z {7, 13, 26, 50, 82}. The number of templates in the library were varied to test the effects of library density on algorithm performance. Two sets of Monte Carlo samples were drawn. The first set was used for training the attraction coefficients and the second set was used for the evaluation. The areal density estimate is considerably better than the estimate of Z. However, this is somewhat deceiving in that many of the poor estimates correspond to samples which a low areal density. As the Z of the shielding material is less important for thin shields, this performance is acceptable.

Source Activity

This method, according to some embodiments, works well to estimate the shielding areal density and Z. However, the activity of the source has not yet been calculated. Several methods of estimating the activity directly were considered; in the same fashion that the areal density was computed. However, the most consistent results were produced by computing the activity based on the estimated Z and areal density (AD). For a given shielding configuration characterized by Z and AD, the dose per unit activity can be computed by table lookup. Tables of these quantities are often used by health physicist to estimate the required shielding on a source material. As was noted previously, the dose can be accurately computed based on the templates used to fit the observation, and therefore these three quantities can be combined to estimate the activity of the source. This method works best, according to some approaches, for point sources with simple source shielding configurations as complex shielding layers or distributed sources tend to produce less acceptable results.

Of course, any metric may be used in order to compute the activity of the source. Dose has been described previously due to the availability of dose tables allowing table lookup. Another metric that can be used is total counts. In either case, a formula that may be used to calculate the metric is of the form: metric=∫(F(E)·C(E)·dE), where F(E) is a metric weighting function and C(E) is the counts. For example, for dose as the metric, the formula would be the integral of the dose factor times the counts, where the dose factor is the detector dependent inverse function based on the effective dose and the detector efficiency. Uniform weighting gives total counts. Any number of weighted spectral counts may be constructed and may be used as the metric. Dose is one example of such as metric, but is not limiting on the embodiments described herein. As previously mentioned, dose is useful because one set of tables can be used for all detectors as the detector dependencies have been removed.

Figure 5:
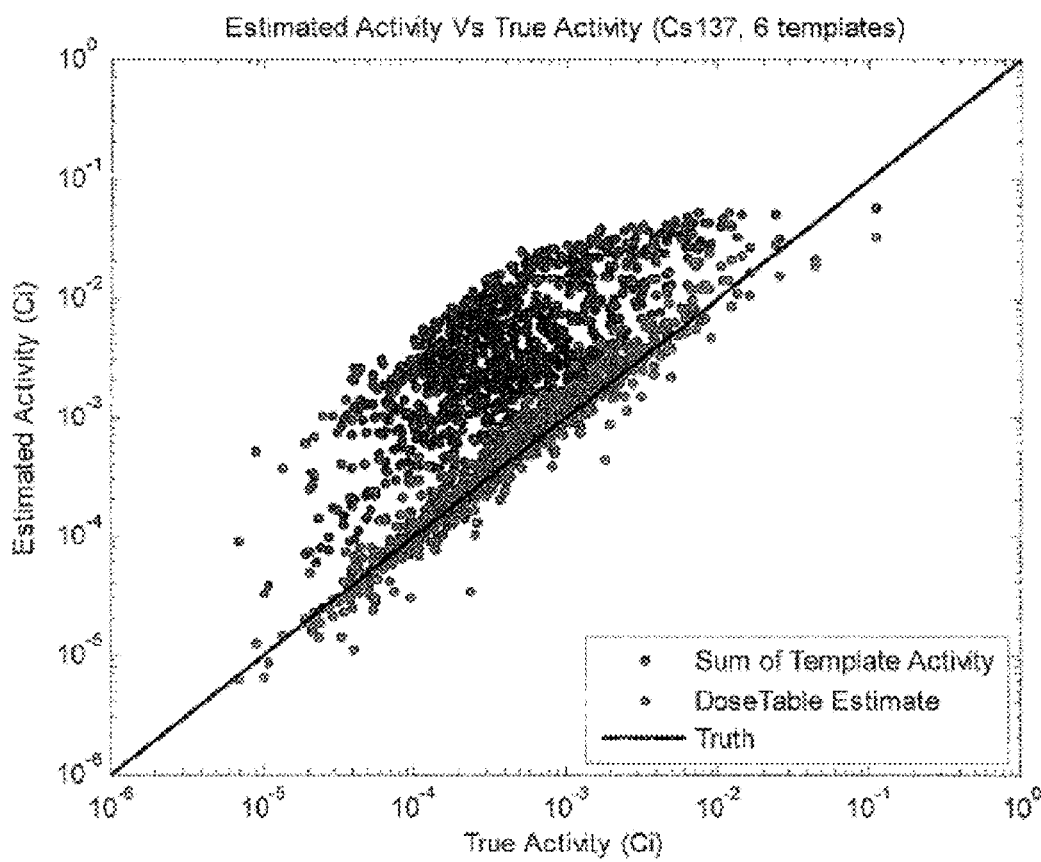
FIG. 5 is a plot of estimated activity versus truth for Monte Carlo evaluation showing both the naïve approach and the dose table approach, according to several embodiments.

This activity estimation algorithm is evaluated using the same evaluation and training procedure as the shielding evaluation. Results of this evaluation appear in FIG. 5, which shows the estimated activity versus true activity for Monte Carlo evaluation showing the naïve and the dose table method, according to some embodiments. In addition to the shielding attraction coefficients, the log of the dose per unit activity tables indexed by effective Z and areal density are pre-computed. A standard linear interpolation was used to compute the dose factor for this demonstration. The count rate is drawn as an independent random variable ranging from 500 to 20,000 for the simulation; thus, the corresponding activity range for different shielding configuration ranges accordingly.

Even with only six templates, the activity estimates for this algorithm are a considerable improvement over estimating by summing the template activities. The mean estimate was only 16% higher than the actual activity with a standard deviation of 38%. The 5th percentile estimate was 0.72 of true activity and the 95th percentile is 1.86 times the true activity over the set. Direct summing of template activity overestimates the activity by 1.9 times in the 5th percentile and 38 times in the 95th percentile. Increasing the number of templates to 15 improves the 95th percentile to 1.66, but this is insignificant compared to the expected uncertainties in source distance; thus, this procedure does not increase the number of templates required. Similar performance has been achieved for $^{192}$Ir, $^{60}$Co, and $^{75}$Se with properly spaced templates.

According to one embodiment, activity, areal density and effective Z for shielding can be computed by calculating an attractor factor for each parameter to be interpolated. For monoenergetic sources, this method uses roughly six templates total, but more or less can be used depending on accuracy sought. The templates increase to two templates for complex multienergy sources such as $^{226}$Ra. For a realistic library covering most radio-nuclides expected in the field, roughly 300 templates may be used. This qualifies as a reasonably compact representation of the expected spectra while providing acceptable estimates of these important physical quantities. The quality of the activity estimate has also been determined to be sufficient enough that it could be used as part of an alarming algorithm.

Now, a method for calculating an activity of a source, according to one embodiment, is described in general terms.

In one embodiment, a probable solution is received, possibly by a processor, a memory, or some other device which is capable of receiving an electronic expression of a probable solution. The probable solution has been predetermined, and may be represented as $S=\{T_i, N_i, x_i\}$, where T is a template/regressor number, N is a radio-nuclide corresponding to the template T, and x is a weighting factor corresponding to the template T and representing the contribution of the radio-nuclide to the probable solution. In some approaches, the probable solution may be determined such that $Y=\Sigma(A_i \cdot x_i)$, where Y is the observation to which the probable solution is determined, A is the activity of the radio-nuclide, and x is the weighting factor.

For each radio-nuclide ($N_p$) in the set $Q=\{N_i==N_p\}$, a numerator and a denominator may be established to calculate an effective areal density ($AD_{eff}$). The numerator ($AD_{num}$) equals the sum of an areal density biasing coefficient ($ADB_j$) times an areal density ($AD_j$) for the specific radio-nuclide (Np) times the weighting factor ($x_j$) for each member of the set Q, or $AD_{num}=\Sigma(ADB_j \cdot AD_j \cdot x_j)$. The denominator ($AD_{den}$) equals the sum of the areal density biasing coefficient ($ADB_j$) times the weighting factor ($x_j$) for each member of the set Q, or $AD_{den}=\Sigma(ADB_j \cdot x_j)$. The effective areal density ($AD_{eff}$) then equals the numerator ($AD_{num}$) divided by the denominator ($AD_{den}$), or $AD_{eff}=AD_{num}/AD_{den}$.

In addition, in some approaches, an effective atomic number ($Z_{eff}$) may be computed from a numerator ($Z_{num}$) and a denominator ($Z_{den}$). A Z biasing coefficient ($ZB_j$) is calculated for each radio-nuclide in the set Q, and an atomic number for each radio-nuclide ($Z_j$) is provided. According to one embodiment, $Z_{num}=\Sigma(ZB_j \cdot Z_j \cdot x_j)$. Also, $Z_{den}=\Sigma(ZB_j \cdot x_j)$, and $Z_{eff}=Z_{num}/Z_{den}$.

In some approaches, dose may be used as a metric from which to compare values in tables. For example, knowing the effective areal density ($AD_{eff}$) and the effective atomic number ($Z_{eff}$), a dose conversion may be calculated as $Dose_{con}=Lookup(AD_{eff}, Z_{eff})$//units activity per unit dose. Then, an activity can be calculated as $Activity(N_p)=Dose \cdot Dose_{con}$.

Figure 6:
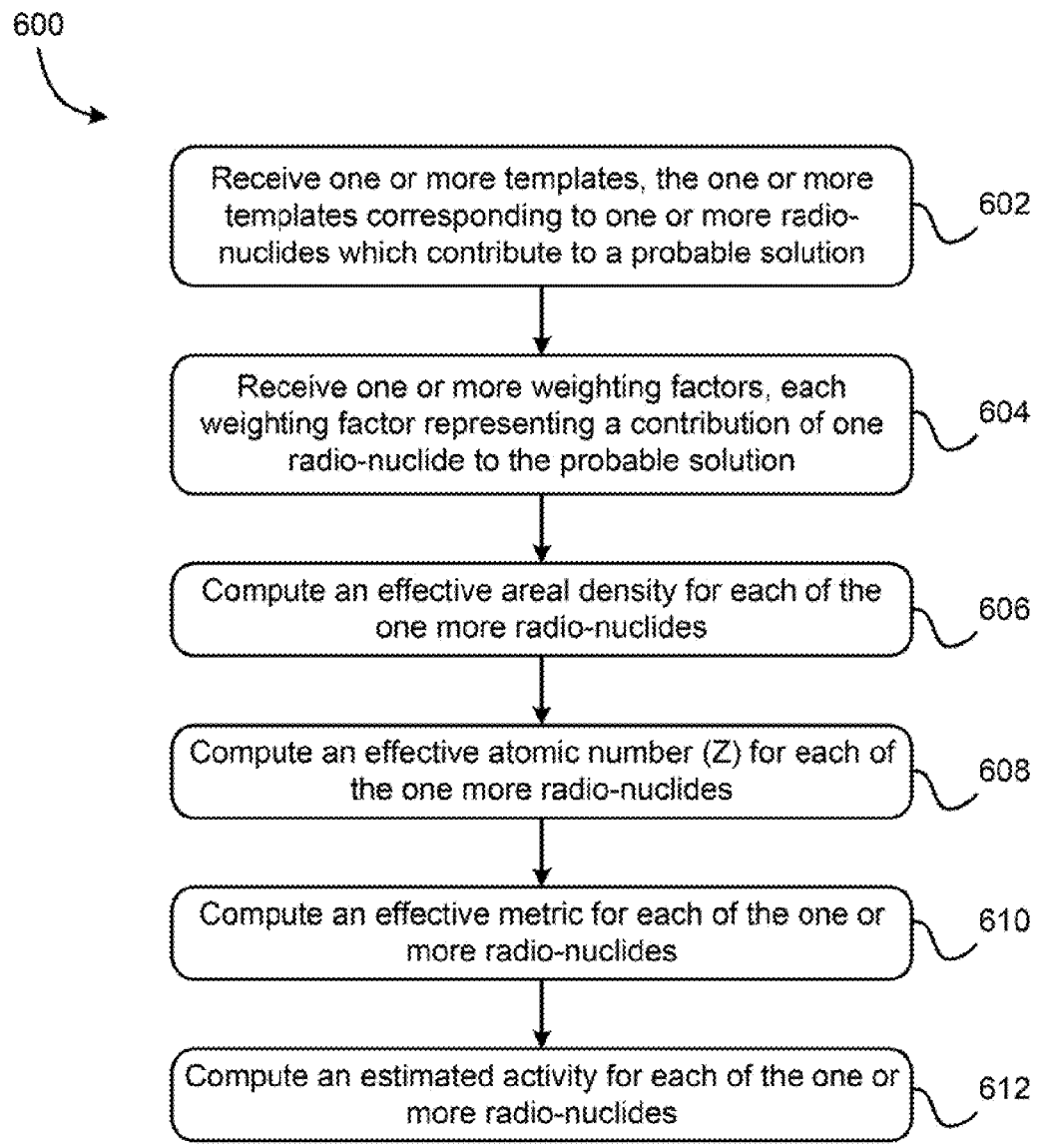
FIG. 6 is a flowchart of a method for estimating an activity of one or more radio-nuclides, according to one embodiment.

Now referring to FIG. 6, a method 600 for estimating an activity of one or more radio-nuclides is described. The method may be carried out in any desired environment, and may rely on other methods from which to gather information from which to perform the operations. Any method capable of producing a set suitable information may be used with the method 600.

In operation 602, one or more templates is received. Each of the received templates corresponds to a radio-nuclide which contributes to a probable solution.

In operation 604, one or more weighting factors are received, each weighting factor representing a contribution of one radio-nuclide to the probable solution.

In some approaches, the probable solution fits the equation $Y=\Sigma(A_i \cdot x_i)$, where Y is the observation to which the probable solution is determined, A is the activity of each radio-nuclide contributing to the probable solution, and x is the weighting factor corresponding to the contribution of each radio-nuclide to the probable solution. The summing is performed across all members of the probable solution (i).

In operation 606, an effective areal density is calculated for each of the one more radio-nuclides. Any method of calculating an effective areal density may be used. In one example, the effective areal density ($AD_{eff}$) equals the numerator ($AD_{num}$) divided by the denominator ($AD_{den}$), or $AD_{eff}=AD_{num}/AD_{den}$, where the numerator ($AD_{num}$) equals the sum of an areal density biasing coefficient ($ADB_j$) times an areal density ($AD_j$) for the specific radio-nuclide (Np) times the weighting factor ($x_j$) for each member of the set Q, or $AD_{num}=\Sigma(ADB_j \cdot AD_j \cdot x_j)$, and the denominator ($AD_{den}$) equals the sum of the areal density biasing coefficient ($ADB_j$) times the weighting factor ($x_j$) for each member of the set Q, or $AD_{den}=\Sigma(ADB_j \cdot x_j)$.

The areal density biasing coefficient ($ADB_j$) may be determined based on observations of the radio-nuclide and how instruments bias readings of the radio-nuclide. The biasing coefficient may then take into account this perceived bias in order to remove any measuring errors from the calculations.

In operation 608, an effective atomic number is calculated for each of the one more radio-nuclides. For example, an effective atomic number ($Z_{eff}$) may be computed from a numerator ($Z_{num}$) and a denominator ($Z_{den}$). A Z biasing coefficient ($ZB_j$) may be calculated for each radio-nuclide in the set Q, and an atomic number for each radio-nuclide ($Z_j$) may be provided. According to one embodiment, $Z_{num}=\Sigma(ZB_j \cdot Z_j \cdot x_j)$. Also, $Z_{den}=\Sigma(ZB_j \cdot x_j)$, and $Z_{eff}=Z_{num}/Z_{den}$.

The Z biasing coefficient ($ZB_j$) may be determined based on observations of the radio-nuclide and how instruments bias readings of the radio-nuclide. The biasing coefficient may then take into account this perceived bias in order to remove any measuring errors from the calculations.

In operation 610, an effective metric is calculated for each of the one or more radio-nuclides. In one embodiment, computing an effective metric ($M_{eff}$) for the one or more radio-nuclides comprises summing each of the effective metrics ($M_j$) multiplied by the weighting factor ($x_j$) for each of the one or more radio-nuclides, $M_{eff}=\Sigma(M_j \cdot x_j)$. According to one embodiment, the metric may be one of dose and total counts. Of course, any other metric may be used, and the metrics described herein are not meant to be limiting on the invention.

In some embodiments, the method 600 further includes obtaining a metric per unit activity for the one or more radio-nuclides by using a lookup table comprising shielding materials, shielding atomic number, shielding areal density, and source materials.

In operation 612, an estimated activity is calculated for each of the one or more radio-nuclides. In one embodiment, computing an estimated activity for the one or more radio-nuclides includes dividing the effective metric by the metric per unit activity to calculate the estimated activity for the one or more radio-nuclides.

In another embodiment, a computer program product may be provided for estimating an activity of one or more radio-nuclides. The computer program product comprises a computer readable memory having computer readable code stored thereon. The computer readable code is configured to: receive one or more templates, the one or more templates corresponding to one or more radio-nuclides which contribute to a probable solution; receive one or more weighting factors, each weighting factor representing a contribution of one radio-nuclide to the probable solution; compute an effective areal density for each of the one more radio-nuclides; compute an effective atomic number (Z) for each of the one more radio-nuclides; compute an effective metric for each of the one or more radio-nuclides; and compute an estimated activity for each of the one or more radio-nuclides.

Any of the above described embodiments relating to method 600 may be incorporated into a computer program product for use with a computer system of some kind.

Figure 7:
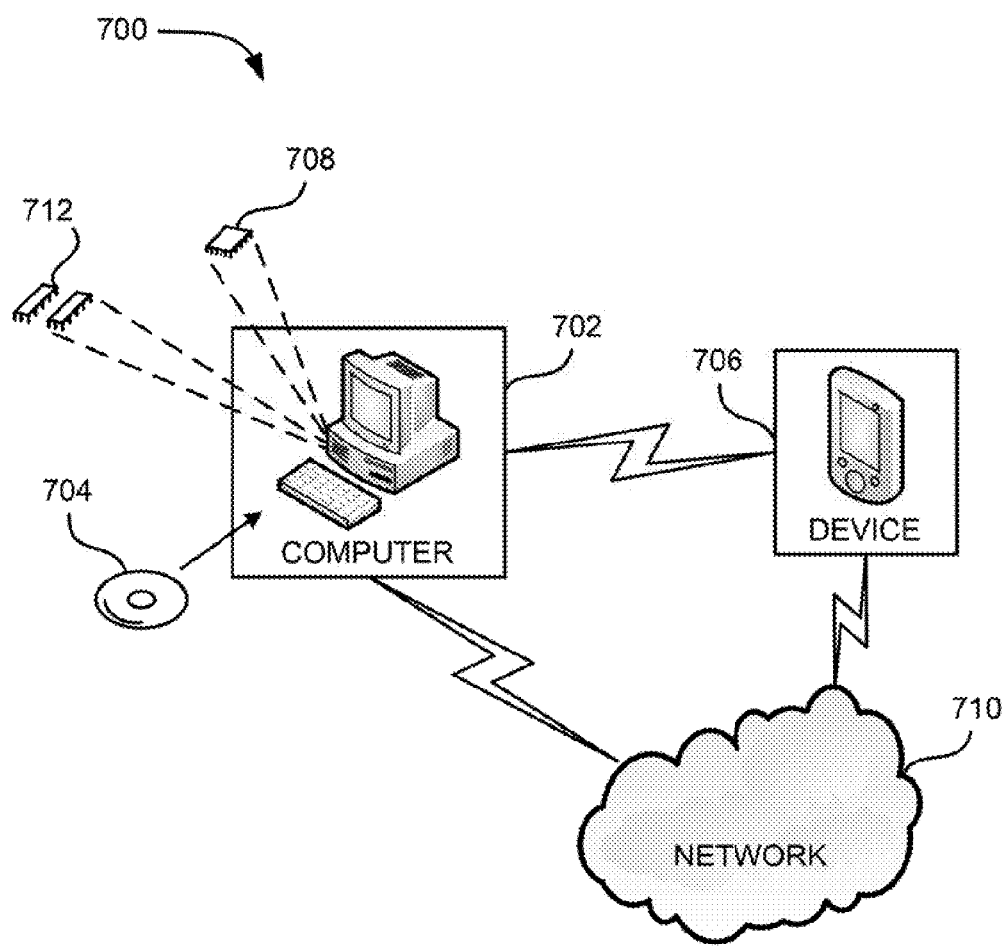
FIG. 7 is a simplified schematic diagram of a computer system, according to one embodiment.

Now referring to FIG. 7, in another embodiment, a system 700 includes a processor 708 for executing computer readable code, which may be part of a larger computer system 702, and a computer readable memory 712. In another embodiment, a computer readable memory 704 may be removable from the system 700, and may include a computer program product. Computer readable code included with the computer readable memories 704, 712, may be executable by the processor 708 or by another device 706, possibly through a connection with a network 710 such as the Internet, a wide area network (WAN), a virtual private network (VPN), a local area network (LAN), etc.

In one embodiment, a system includes a processor; a computer readable memory; and logic, which when executed by the processor causes the system to perform functions. The functions include receiving one or more templates, the one or more templates corresponding to one or more radio-nuclides which contribute to a probable solution; receiving one or more weighting factors, each weighting factor representing a contribution of one radio-nuclide to the probable solution; computing an effective areal density for each of the one more radio-nuclides by calculating an areal density biasing coefficient for each of the one or more templates; multiplying together the weighting factor for each of the one or more radio-nuclides, the areal density biasing coefficient for each of the one or more templates, and an areal density corresponding to each of the one or more template to obtain a value; and dividing the value by a sum of the weighting factors for each of the one or more radio-nuclides multiplied by the areal density biasing coefficient for each of the one or more templates; computing an effective atomic number (Z) for each of the one more radio-nuclides by calculating an effective atomic number (Z) biasing coefficient for each of the one or more radio-nuclides; multiplying, for each of the one or more radio-nuclides, the weighting factor by the effective atomic number (Z) biasing coefficient by an atomic number (Z) corresponding to each of the one or more templates to obtain a value; and dividing the value by a sum of the weighting factors for each of the one or more radio-nuclides multiplied by the effective atomic number (Z) biasing coefficient; computing an effective metric for each of the one or more radio-nuclides by summing each of the effective metrics multiplied by the weighting factor for each of the one or more radio-nuclides; and computing an estimated activity for each of the one or more radio-nuclides by dividing the effective metric by a metric per unit activity to calculate the estimated activity for the one or more radio-nuclides.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for estimating an activity of one or more radio-nuclides, the method comprising:
   receiving one or more templates, the one or more templates corresponding to one or more radio-nuclides which contribute to a probable solution;
   receiving one or more weighting factors, each weighting factor representing a contribution of one radio-nuclide to the probable solution;
   computing an effective areal density for each of the one more radio-nuclides;
   computing an effective atomic number (Z) for each of the one more radio-nuclides;
   computing an effective metric for each of the one or more radio-nuclides; and
   computing, using a processor, an estimated activity for each of the one or more radio-nuclides based at least in part on one or more of:
   one or more of the one or more weighting factors;
   one or more biasing coefficients;
   the effective areal density for each of the one or more radio-nuclides;
   the effective atomic number (Z) for each of the one or more radio-nuclides; and
   the effective metric for each of the one or more radio-nuclides.

2. The method of claim 1, further comprising calculating the one or more biasing coefficients for each of the one or more radio-nuclides based on observations of the one or more radio-nuclides, wherein calculating one or more of the effective areal density and the effective atomic number is based at least in part on the one or more biasing coefficients.

3. The method of claim 1, Wherein computing an effective areal density for each of the one more radio-nuclides comprises:
   calculating an areal density biasing coefficient for each of the one or more templates;
   multiplying together the weighting factor for each of the one or more radio-nuclides, the areal density biasing coefficient for each of the one or more templates, and an areal density corresponding to each of the one or more templates to obtain a value; and
   dividing the value by a sum of the weighting factors for each of the one or more radio-nuclides multiplied by the areal density biasing coefficient for each of the one or more templates.

4. The method of claim 1, wherein computing an effective atomic number (Z) for each of the one more radio-nuclides comprises:
   calculating an effective atomic number (Z) biasing coefficient for each of the one or more radio-nuclides;
   multiplying, for each of the one or more radio-nuclides, the weighting factor by the effective atomic number (Z) biasing coefficient by an atomic number (Z) corresponding to each of the one or more templates to obtain a value; and
   dividing the value by a sum of the weighting factors multiplied by the effective atomic number (Z) biasing coefficient for each of the one or more radio-nuclides.

5. The method of claim 1, Wherein computing an effective metric for the one or more radio-nuclides comprises summing each of the effective metrics multiplied by the weighting factor for each of the one or more radio-nuclides.

6. The method of claim 1, further comprising obtaining a metric per unit activity for the one or more radio-nuclides by using a lookup table comprising shielding materials, shielding atomic number, shielding areal density, and source materials.

7. The method of claim 6, wherein computing an estimated activity for the one or more radio-nuclides comprises dividing the effective metric by the metric per unit activity to calculate the estimated activity for the one or more radio-nuclides.

8. The method of claim 1, wherein the effective metric is chosen from a group consisting of dose and total counts.

9. The method as recited in claim 1, wherein computing an estimated activity for each of the one or more radio-nuclides is detector-independent.

10. The method as recited in claim 1, further comprising performing multiple linear regression to determine a combination of pre-computed templates having a best fit to an observed spectrum.

11. The method as recited in claim 1, wherein computing the effective areal density for each of the one or more radio nuclides is based at least in part on one or more of:
an areal density of one or more of the one or more radio-nuclides;
one or more of the one or more weighting factors; and
an areal density biasing coefficient, and
wherein computing the effective atomic number for each of the one or more radio nuclides is based at least in part on one or more of:
an atomic number of one or more of the one or more radio-nuclides;
one or more of the one or more weighting factors; and
a Z biasing coefficient, and
wherein computing the effective areal metric for each of the one or more radio nuclides is based at least in part on one or more of:
a metric fbr one or more of the one or more radio nuclides; and
one or more of the one or more weighting factors.

12. A computer program product for estimating an activity of one or more radio-nuclides, the computer program product comprising:
a non-transitory computer readable medium having computer readable code stored thereon, the computer readable code comprising:
computer readable code configured to receive one or more templates, the one or more templates corresponding to one or more radio-nuclides which contribute to a probable solution;
computer readable code configured to receive one or more weighting factors, each weighting factor representing a contribution of one radio-nuclide to the probable solution;
computer readable code configured to compute an effective areal density for each of the one more radio-nuclides;
computer readable code configured to compute an effective atomic number (Z) for each of the one more radio-nuclides;
computer readable code configured to compute an effective metric for each of the one or more radio-nuclides; and
computer readable code configured to compute an estimated activity for each of the one or more radio-nuclides based at least in part on one or more of:
one or more of the one or more weighting factors;
one or more biasing coefficients;
the effective areal density for each of the one or more radio-nuclides;
the effective atomic number (Z) for each of the one or more radio-nuclides; and
the effective metric for each of the one or more radio-nuclides.

13. The computer program product of claim 12, wherein the computer readable code further comprises computer readable code configured to calculate one or more biasing coefficients for each of the one or more radio-nuclides based on observations of the one or more radio-nuclides.

14. The computer program product of claim 12, wherein the computer readable code configured to compute an effective areal density for each of the one more radio-nuclides comprises:
computer readable code configured to calculate an areal density biasing coefficient for each of the one or more templates;
computer readable code configured to multiply together the weighting factor for each of the one or more radio-nuclides, the areal density biasing coefficient for each of the one or more templates, and an areal density corresponding to each of the one or more template to obtain a value; and
computer readable code configured to divide the value by a sum of the weighting factors for each of the one or more radio-nuclides multiplied by the areal density biasing coefficient for each of the one or more templates.

15. The computer program product of claim 12, wherein the computer readable code configured to compute an effective atomic number (Z) for each of the one more radio-nuclides comprises:
computer readable code configured to calculate an effective atomic number (Z) biasing coefficient for each of the one or more radio-nuclides;
computer readable code configured to multiply, for each of the one or more radio-nuclides, the weighting factor by the effective atomic number (Z) biasing coefficient by an atomic number (Z) corresponding to each of the one or more templates to obtain a value; and
computer readable code configured to divide the value by a sum of the weighting factors for each of the one or more radio-nuclides multiplied by the effective atomic number (Z) biasing coefficient.

16. The computer program product of claim 12, wherein the computer readable code configured to compute an effective metric for the one or more radio-nuclides comprises computer readable code configured to sum each of the effective metrics multiplied by the weighting factor for each of the one or more radio-nuclides.

17. The computer program product of claim 12, further comprising computer readable code configured to obtain a metric per unit activity for the one or more radio-nuclides by using a lookup table comprising shielding materials, shielding atomic number, shielding areal density, and source materials.

18. The computer program product of claim 17, wherein the computer readable code configured to compute an estimated activity for the one or more radio-nuclides comprises computer readable code configured to divide the effective metric by the metric per unit activity to calculate the estimated activity for the one or more radio-nuclides.

19. The computer program product of claim 12, wherein the effective metric is chosen from a group consisting of dose and total counts.

20. A system for estimating an activity of one or more radio-nuclides, the system comprising:
a processor;
a computer readable memory; and
logic, which when executed by the processor causes the system to:
receive one or more templates, the one or more templates corresponding to one or more radio-nuclides which contribute to a probable solution;
receive one or more weighting factors, each weighting factor representing a contribution of one radio-nuclide to the probable solution;
compute an effective area density for each of the one more radio-nuclides by calculating an areal density biasing coefficient for each of the one or more templates; multiplying together the weighting factor for each of the one or more radio-nuclides, the areal density biasing coefficient for each of the one or more templates, and an areal density corresponding to each of the one or more template to obtain a value; and dividing the value by a sum of the weighting factors for each of the one or more radio-nuclides multiplied by the areal density biasing coefficient for each of the one or more templates;

compute an effective atomic number (Z) for each of the one more radio-nuclides by calculating an effective atomic number (Z) biasing coefficient for each of the one or more radio-nuclides; multiplying, for each of the one or more radio-nuclides, the weighting factor by the effective atomic number (Z) biasing coefficient by an atomic number (Z) corresponding to each of the one or more templates to obtain a value; and dividing the value by a sum of the weighting factors for each of the one or more radio-nuclides multiplied by the effective atomic number (Z) biasing coefficient;

compute an effective metric for each of the one or more radio-nuclides by summing each of the effective metrics multiplied by the weighting factor for each of the one or more radio-nuclides; and compute an estimated activity for each of the one or more radio-nuclides by dividing the effective metric by a metric per unit activity to calculate the estimated activity for the one or more radio-nuclides.

* * * * *